(12) United States Patent
Rapp et al.

(10) Patent No.: US 6,602,464 B1
(45) Date of Patent: Aug. 5, 2003

(54) METHOD AND APPARATUS FOR TREATING DIGESTIBLE AND ODIFEROUS WASTE

(76) Inventors: Gary L. Rapp, R.R. #1, Box 177, Athens, IL (US) 62613; Carrie L. Rapp, R.R. #1, Box 177, Athens, IL (US) 62613

( * ) Notice: Subject to any disclaimer, the term of this patent is extended or adjusted under 35 U.S.C. 154(b) by 0 days.

(21) Appl. No.: 09/678,064

(22) Filed: Oct. 2, 2000

Related U.S. Application Data

(60) Provisional application No. 60/197,270, filed on Apr. 14, 2000.

(51) Int. Cl.$^7$ .............................................. A61L 9/014
(52) U.S. Cl. ............................... 422/5; 422/41; 422/42
(58) Field of Search ................................. 422/5, 41, 42; 528/230; 119/1; 222/166; 137/15.04, 15.05, 247.21

(56) References Cited

U.S. PATENT DOCUMENTS

| | | | | |
|---|---|---|---|---|
| 3,639,258 A | * | 2/1972 | Corino et al. ................ | 252/316 |
| 4,007,262 A | * | 2/1977 | Bowers ........................ | 424/76 |
| 4,244,061 A | * | 1/1981 | Webster et al. .............. | 4/144.1 |
| 4,264,760 A | * | 4/1981 | Meyer ......................... | 528/230 |
| 4,641,605 A | * | 2/1987 | Gordon ........................ | 119/1 |
| 4,821,677 A | | 4/1989 | Harrison | |
| 5,772,722 A | | 6/1998 | Gednalske et al. | |
| 5,962,001 A | * | 10/1999 | Rose et al. .................. | 424/404 |

FOREIGN PATENT DOCUMENTS

| | | | |
|---|---|---|---|
| GB | 2296514 A | * | 7/1996 |
| JP | 58013817 A | * | 1/1996 |
| JP | 10167866 A | * | 6/1998 |

OTHER PUBLICATIONS

Clanton et al., "Experiment manure Storgae Covers for Odor Control", www.bae.umn.edu/annrpt/1997/research/odor5.html (1997).*
Camberato et al., "Land Application of Animal Manure", http://hubcap.clemson.edu/~blpprt/manure.html (1996).*
English translation of Yusuaki (JP 1016786). The Examiner previously cited this reference, untranslated, in connection with the First Office Action.
Advertisement for Barrier odor migration aid, Nov. 2000.

\* cited by examiner

Primary Examiner—Robert J. Warden, Sr,
Assistant Examiner—Sean E. Conley
(74) Attorney, Agent, or Firm—H. Frederick Rusche; Robert Muir

(57) ABSTRACT

A method and apparatus are provided for minimizing the emissions of odorous gases and fatty acids generated by digestible and odiferous waste. The apparatus includes a treatment comprising oil, activated carbon and a base buffering agent. The apparatus also includes a system for delivering the treatment through a low pressure output, such as a low pressure manifold with a plurality of delivery pipes. A starter plank made of concrete, used for mounting the apparatus on a wall and a flotation board, made of foamed polystyrene board, directs the flow of the treatment onto the surface of the waste. The method includes the steps of applying oil and activated carbon to the surface of liquid waste and injecting a base buffering agent below the surface of the oil/activated carbon layer. The oil and activated carbon create a seal that prevents odorous emissions from entering the air space above the liquid waste and the base buffering system neutralizes the acidic waste.

20 Claims, 7 Drawing Sheets

METHOD AND APPARATUS FOR TREATING DIGESTIBLE AND ODIFEROUS WASTE

CROSS-REFERENCES

This application claims the priority of co-pending provisional application Ser. No. 60/197,270, filed Apr. 14, 2000.

TECHNICAL FIELD

The present invention relates generally to the field of wastewater treatment and, more particularly, to dealing with odors emitted by organic waste.

BACKGROUND OF THE INVENTION

Over the past decades there has been a shift from smaller localized family farms toward larger integrated confinement agricultural operations. Large agricultural operations typically utilize confinement barns to house a large number of livestock such as swine. It is not uncommon for hog-confinement operations to be grouped in close proximity, forming "mega-farms" which may house tens of thousands of hogs. While these larger agricultural operations have numerous advantages, they also encounter significant pollution problems arising from the handling and treatment of manure and wastewater. Pollution problems associated with liquid animal waste include nitrogen, phosphorus, solids, bacteria and foul odors that result from anaerobic digestion. Environmental concerns more specifically center on odor and water quality issues.

Currently, for treatment of animal wastes and wastewater most agricultural facilities use anaerobic digestion, i.e. anaerobic bacteria consume some or much of the organic waste. The primary reason for using anaerobic digestion is that it is natural but it also has the advantages of simplicity and low cost. Wastewater is simply discharged from the animal storage facility into one or more open lagoons where the waste undergoes natural anaerobic digestion. However, noxious gases including ammonia, methane, hydrogen sulfide, fatty acids, and indoles may be emitted from anaerobic lagoons at hog farms as well as within the animal storage facilities. Additionally, the time required for complete digestion of the organic wastes is relatively long, typically lasting from weeks to months. Some current regulations require a residence time of 180 days for animal waste facilities using anaerobic lagoons for digestion. Odors emanating from lagoons, confinement houses, and fields onto which wastes are sprayed create a nuisance. In fact, as a result of odor problems associated with anaerobic lagoons, some states have legally mandated buffer zones or designated land areas between lagoon sites and populated areas. In addition, the noxious gases produced by animal waste create a potentially hazardous environment in animal storage facilities for humans working in such facilities and the animals housed in these facilities.

Hog lagoon liquid effluent characteristically has high levels of nitrogen and phosphorus that cannot be decreased to acceptable levels by anaerobic treatment alone. Even with bacterial digestion, significant amounts of sludge accumulate in an anaerobic lagoon. Anaerobic lagoons may fill to capacity fairly quickly which displaces the designed retention capacity of the lagoon fairly quickly and often serve to provide only partial pretreatment. Often, anaerobic settling lagoons serve to separate solids and reduce or decompose wastes enough to land spread or spray the waste on irrigation fields.

Continuing efforts are being made to improve agricultural and animal waste treatment methods and apparatus. For example, one process known in the art is the transformation of animal waste wherein solids are precipitated in a solids reactor, the treated slurry is passed to a bioreactor zone where soluble phosphorus is precipitated with metallic salts, the slurry is aerobically and anaerobically treated to form an active biomass. The aqueous slurry containing bio-converted phosphorus is passed into a polishing eco-reactor zone wherein at least a portion of the slurry is converted to a beneficial humus material. However, in operation, the system requires numerous chemical feeds and a series of wetland cells comprising microorganisms, animals and plants.

Several studies done in the past several years have also addressed the issue of reducing odors by covering manure storage units. For example, many types of natural floating covers formed by fibrous materials have been used to reduce manure odor. Artificial floating crusts have consisted of chopped straw, plastic foam pellets, a combination of straw and pellets, mats, or tarpaulins. Tight covers have included plastic covers sealed at the edge and light constructed roofs. These types of covers have proven to be inadequate for several reasons. Such covers have not sufficiently eliminated odorous emissions. Also, such covers cannot be efficiently utilized in an animal storage facility, where the pit must remain open to receive waste as it is generated by the housed animals. Natural floating covers have also been known to fail under conditions such as rainy weather, which causes the floating crusts to become submerged in the waste.

SUMMARY OF THE INVENTION

The present invention provides a method and apparatus for treatment of agricultural animal waste to minimize odorous emissions. The treatment includes a layer of oil, preferably vegetable oil, and activated carbon applied to the surface of liquid animal waste. The ratio of oil to activated carbon is preferably approximately 5:1. This layer of treatment creates a seal that inhibits the emission of odorous gases. Even when exposed to rain, the oil/activated carbon layer keeps the liquid waste odors sealed.

The treatment also includes the injection of a base buffering agent into the liquid waste, below the oil/activated carbon layer. This base buffering agent neutralizes the acidic liquid animal waste, thereby minimizing the odorous gases, emitted from the liquid waste. The addition of the base buffering agent is controlled to prevent the occurrence of an excessively high pH level in the waste. This is necessary to maintain the anaerobic environment within the treated waste, which is required for the treatment to work.

The present invention includes an applicator system for applying the treatment to the liquid animal waste without agitating the waste beneath the surface oil/activated carbon layer. This is necessary because agitation of the waste beneath the surface causes gases and odors to be emitted.

The present invention also includes a retainer system which prevents the treatment from being pumped away with the liquid waste during emptying of a treated animal waste pit. This system is advantageous to the extent that it allows the treatment to be retained after pumping away the liquid waste, thereby obviating the need to apply a new treatment after each emptying of the waste pit.

The present invention provides many advantages, including reducing emission of odorous gases, stopping the evaporation of liquids beneath the surface of the treatment to reduce the humidity levels in animal storage facilities, maintaining higher quality of air in animal storage facilities, liquefying waste solids through bacterial activity and the establishment of an anaerobic environment, maintaining the seal above the liquid waste because any of the treatment dragged below the surface by waste falling on the treatment surface layer automatically reemerges at the surface, improving feed quality as moisture and airborne bacteria growth is reduced, reducing harmful dust particles in the animal waste environment, stopping erosion in lagoons by inhibiting agitation of the liquid waste, and reducing airborne bacteria which causes and spreads infectious diseases.

BRIEF DESCRIPTION OF THE DRAWINGS

Reference is now made to the drawings which illustrate the best known mode of carrying out the invention and wherein the same reference numerals indicate the same or similar parts throughout the several views.

DESCRIPTION OF THE PREFERRED EMBODIMENTS

Figure 1:
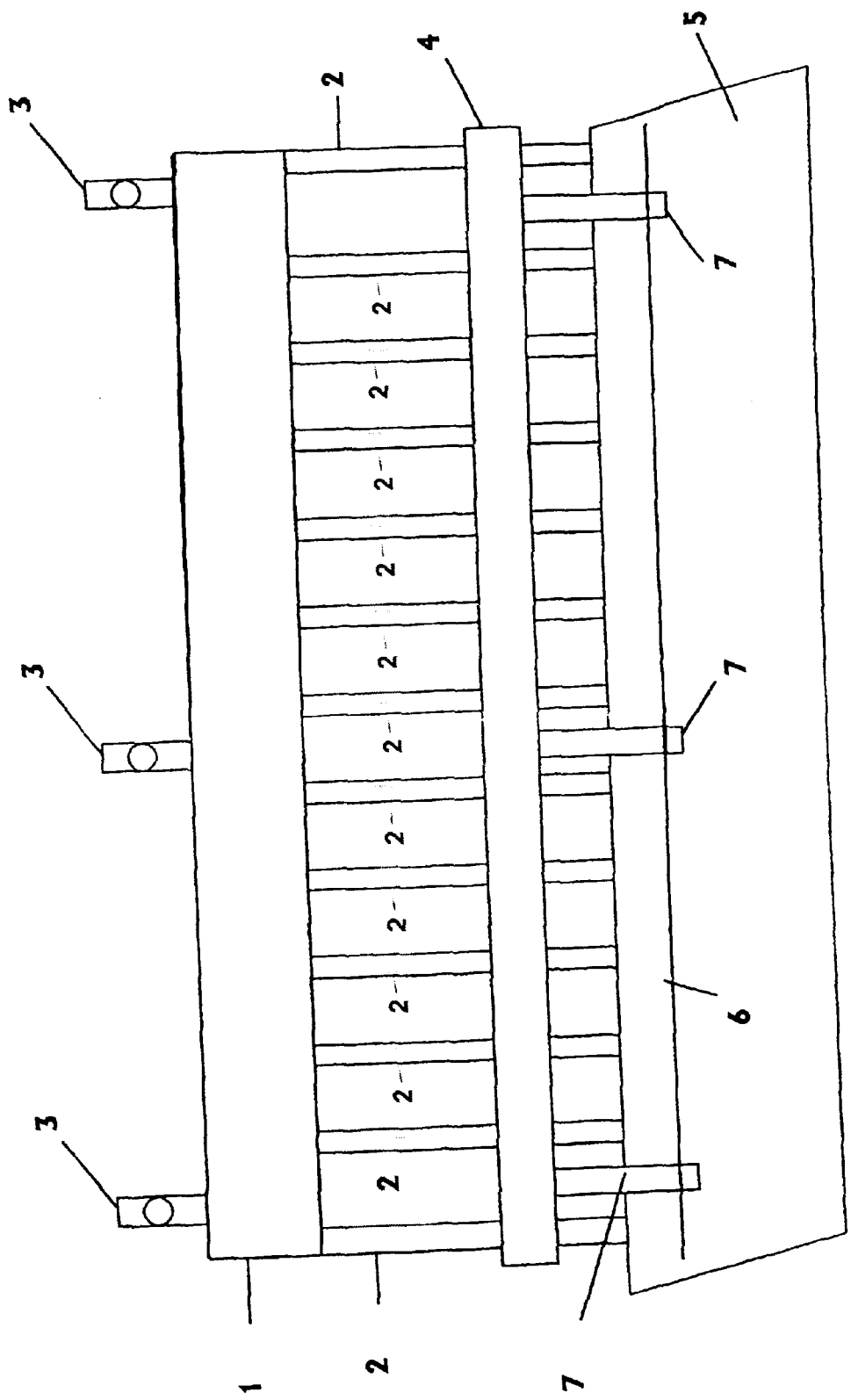
FIG. 1 is a front view of an applicator system.

A system and/or process in accordance with present invention treats an agricultural animal waste 16 to minimize the escape of odors from waste gases that are emitted into the air from agricultural animal waste 16 storage pits or waste lagoons, and thereby reduces offensive odors present for detection by the human nose. It has been found that a layer of oil covering the surface of the pit or lagoon effectively reduces the offensive odors. For convenience this layer is sometimes hereafter referred to as an "oil seal". The oil seal provides an anaerobic environment advantageous for digestion of the organic waste. Advantageously the oil layer may also be combined with either the activated carbon or a base buffering agent. While these combinations effectively reduce offensive odors, preferred results are obtained by using a combination all three elements.

In accordance with a preferred embodiment, the oil is preferably a vegetable oil combined with activated carbon, and the base buffering agent is preferably ammonia ($NH_3$) with ammonium chloride ($NH_4Cl$). In one preferred embodiment, the oil to activated carbon ratio is. approximately 5:1. The base buffering agent is applied beneath the surface of an oil/activated carbon layer 15, to control the pH of the waste 16 and to reduce the concentration of fatty acids and hydrogen sulfide ($H_2S$). The base in the buffer neutralizes the fatty acids and hydrogen sulfide to less volatile salts, which remain in the waste 16. Accordingly, the emission of $H_2S$ and other odorous gases is significantly lowered. The vegetable oil is applied at a thickness, preferably a layer of at least one inch, that more or less provides a seal above the animal waste 16 when applied. The activated carbon provides a trap for gases emitted from the animal waste 16 located beneath the surface of the oil.

One preferred method for treating animal waste 16 in a pit includes the step of first pumping the pit to the lowest level possible, using normal means of extraction that are well-known in the art. If pumping and delivering of the waste 16 to an approved disposal area is not possible, the method can nonetheless be carried out without first pumping the pit. The next step is to apply preferably a one-inch layer of the oil/activated carbon mixture to the surface of the remaining waste 16 in the pit. Next, the base buffering agent is injected below the oil/activated carbon layer 15. The pit is now ready to receive quantities of untreated waste. Once the waste 16 reaches a level in the pit which requires the pit to be pumped again, the pit may once again be pumped. However, the oil/activated carbon will remain on the surface if the waste 16 is pumped from the bottom of the pit. Thus, the need to apply an additional treatment of oil and activated carbon each time the pit is pumped is greatly reduced or eliminated.

It is important that the oil, activated carbon and base buffering agent are applied to the waste 16 such that the waste 16 is not agitated. Agitation of the waste 16 beneath the surface layer 15 causes gases and odors to be emitted, which has been known to result in death to livestock as well as humans. Therefore, it is advantageous to use an appropriate applicator system in applying the treatment.

One preferred applicator system is shown in FIG. 1. The preferred applicator system advantageously uses a high pressure input, generated by a pump, with a low pressure output, such as a low pressure manifold 1 with a plurality of delivery pipes 2. A plurality of mounting brackets 3 are secured to the low pressure manifold 1 and provide a means for mounting the low pressure manifold 1 to the wall of the building housing the animal waste 16. The low pressure manifold 1 reduces the pressure of the high pressure input to low pressure output by allowing the treatment to be discharged from a plurality of discharge points. A starter plank 4, constructed preferably of reinforced concrete, is used to replace a small section of the flooring for the purpose of mounting the applicator system at an end wall near the end of the pit area. A floatation board 5, preferably made of foamed polystyrene board, is also provided to direct low pressure flow of the treatment onto the surface of the waste 16. As the treatment is discharged from the delivery pipes 2 onto the top of the floatation board 5, it slowly runs off to the surface of the liquid waste 16 in the pit. A hinge rod 6, preferably constructed of polyvinyl chloride (PVC) plastic, is mounted through the floatation board 5 and acts as a hinge point, allowing the floatation board 5 to ride with the waste 16 level of the pit. A plurality of pivot points 7, preferably made of PVC plastic, are embedded in the bottom of the starter plank 4 and are used for the floatation hinge rod 6 to be inserted through the flotation board 5. A plurality of delivery pipes 2 are connected to the bottom of the low pressure manifold 1 and provide a path for the treatment beneath the starter plank 4 and onto the floatation board 5.

The system shown is arranged so that a quick coupler (not shown) can be easily connected outside a building being treated, or to the discharge line of a trailer (not shown) containing a supply of oil, or oil and activated carbon mixture, herein sometimes called the "treatment". The treatment is delivered from the trailer or other appropriate storage means directly into the pit. Also, a flow meter may be advantageously used to monitor the amount of treatment that is being delivered.

Figure 2:
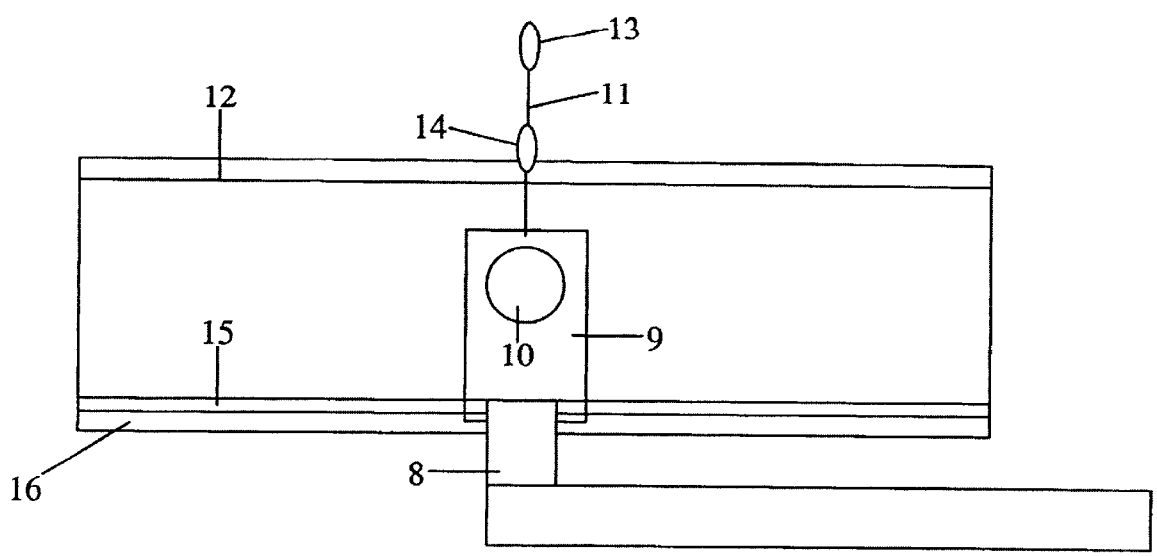
FIG. 2 is a front view of a treatment retainer system.

It is also advantageous to maintain the oil/activated carbon layer 15 in the pit after pumping the waste 16 from the pit being treated. For this purpose a treatment retainer system is provided. As shown in FIG. 2, the retainer system includes a drain pipe 8 through which the animal waste 16 travels as it is pumped out of the pit, a vent pipe 9 which is secured to the drain pipe, a ball 10 which is used to keep the waste 16 from traveling through the drain pipe 8 during normal operation, a pull cable 11 connected to the ball 10 for lifting the ball 10 from the drain pipe 8 to allow the animal waste 16 to exit through the drain pipe 8 to a lagoon or other suitable waste containment destination, and flooring 12 upon which the animals may move freely about. The pull cable 11 is attached at one end to the ball 10 and is attached at its other end to a pull link 13. The pull link 13 allows the operator to lift the ball 10 and drain the waste from the pit. A retainer link 14 is also attached to the cable 11, between the pull link 13 and the ball 10. The retainer link 14 provides a means for easily accessing the cable 11 above the flooring 12, allowing for the pulling of the ball 10 and draining of the pit, while keeping the flooring 12 free from obstructions that would prohibit the movement of the animals. The vent pipe 9 advantageously allows air to draft downwards as the flow of the waste is being drawn from the pit by means of the drain pipe 8. The vent pipe 9 may be advantageously secured to the drain pipe 8 by struts and a clamp (not shown) that encompass the drain pipe 8. The vent 9 also advantageously provides a separation of the oil/activated carbon layer 15 from coming into contact with the drain pipe 8, thereby preventing the oil/activated carbon layer 15 from being drained out of the pit with the waste 16. Once the level of the oil/activated carbon layer 15 is equal to the top of the drain pipe 8, all drainage stops.

The following tests illustrate the effectiveness of the odor control. Samples were tested in an environment that simulated conditions found in animal storage facilities. A general exhaust system was utilized in the laboratory tests. Two testing rooms of equal size and air space were provided for testing. One sample was poured and left untreated as a base-line or control sample, and another sample of equal volume and surface area was treated in accordance with the above description. The samples were contained in a rectangular tray. Raw swine waste extracted from a finishing barn was used for the samples to produce the odors. A depth of 1.5 inches of waste was applied in each tray. After applying the treatment to the surface of said other sample, the prepared samples were left to stand for four minutes. Then each sample was placed in the center of the designated room for the purpose of creating an air sample to be tested initially by smell. In the room where the untreated sample was left, odors were detected immediately upon entering the room and before the sample could be tested. In the room containing the treated sample, no odors were detected in the presence of the sample; indeed the room appeared to smell the same as before the treated sample was placed therein.

The samples were left in the testing areas for 24 hours and once again the rooms were monitored for the presence of odor. In the room where the untreated sample was left, the odors were still present at an unacceptable level. In the room where the treated sample was left, there was no odor present that was detectable by the human nose.

Figure 3:
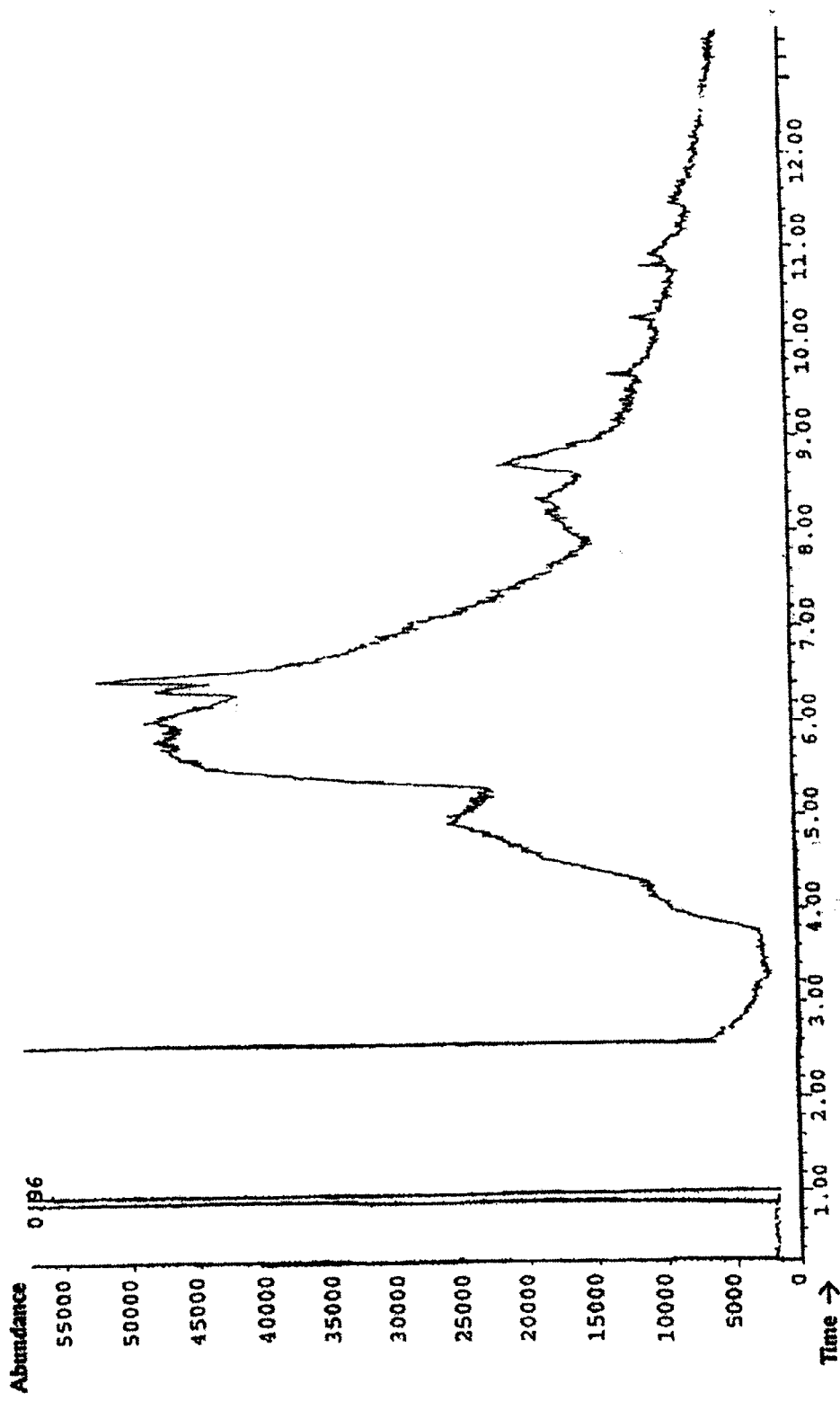
FIG. 3 is a chromatograph of a sample collected above an untreated portion of a concentrated acid solution

Further testing was conducted using gas chromatography—mass spectroscopy (GS-MS) to detect the presence of odiferous compounds. Several pure volatile fatty acids, i.e., acetic acid, propionic acid, butanoic acid, haxanoic acid and heptanoic acid, were mixed together with small amounts of water to produce an aqueous solution far more concentrated in volatile fatty acids than in animal waste slurry 16. Because of the high concentration of these fatty acids in aqueous solution, the same acids could be detected by gas chromatography—mass spectroscopy in the headspace above the liquid sample. FIG. 3 shows the results collected from the sealed headspace above an untreated portion of the concentrated acid solution. The greater the area under a peak shown in FIG. 3, the higher the concentration of the compound being detected in the headspace. The signals recorded beyond 3.5 minutes are due to acetic acid (4.0–5.0 min.), propionic acid (4.5–5.5 min.), butanoic acid (5.5–8.0 min.) and hexanoic acid (7.0–10 min.). Heptanoic acid was not detected in the headspace. The signal before 3.0 minutes, which goes off the chart shown in FIG. 3, is due to argon and carbon dioxide. Both argon and carbon dioxide are minor components of the natural air we breath. Thus, the graph in FIG. 3 demonstrates how low in concentration the fatty acids are, even above a very concentrated solution. However, even a relatively low concentration of fatty acids in the headspace may create a highly offensive odor and potentially dangerous odorous emissions.

Figure 4:
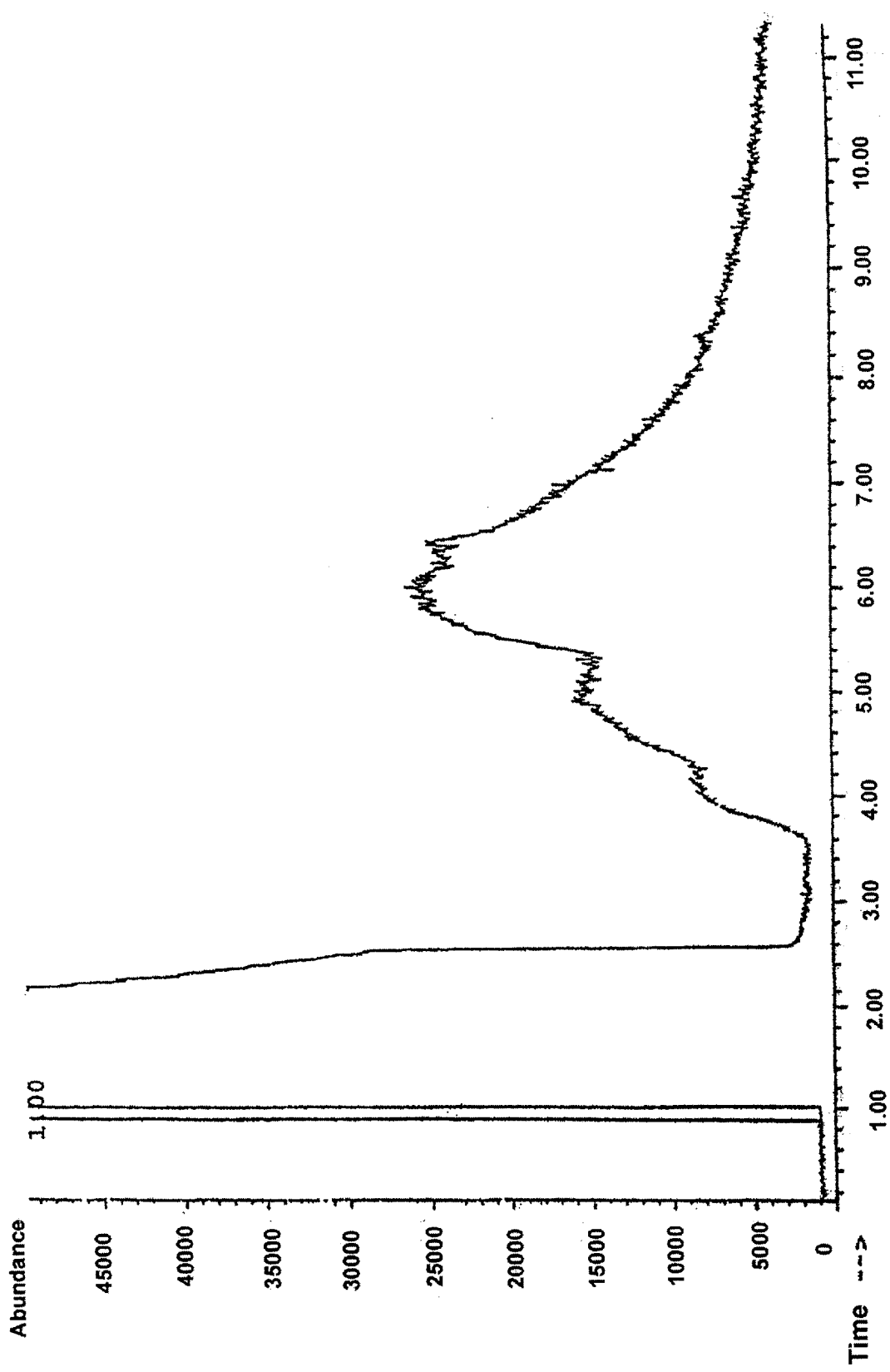
FIG. 4 is a chromatogram of a sample collected above a concentrated fatty acid solution covered with one inch of an oil.

FIG. 4 is the chromatogram of a sample collected above the same concentrated fatty acid solution, now covered with one inch of corn oil alone, and shows the reduction in the areas under the peaks for all the fatty acids. What is seen in the first few minutes on FIG. 4 is merely background noise, which can be shown to be void of the fatty acids.

Figure 5:
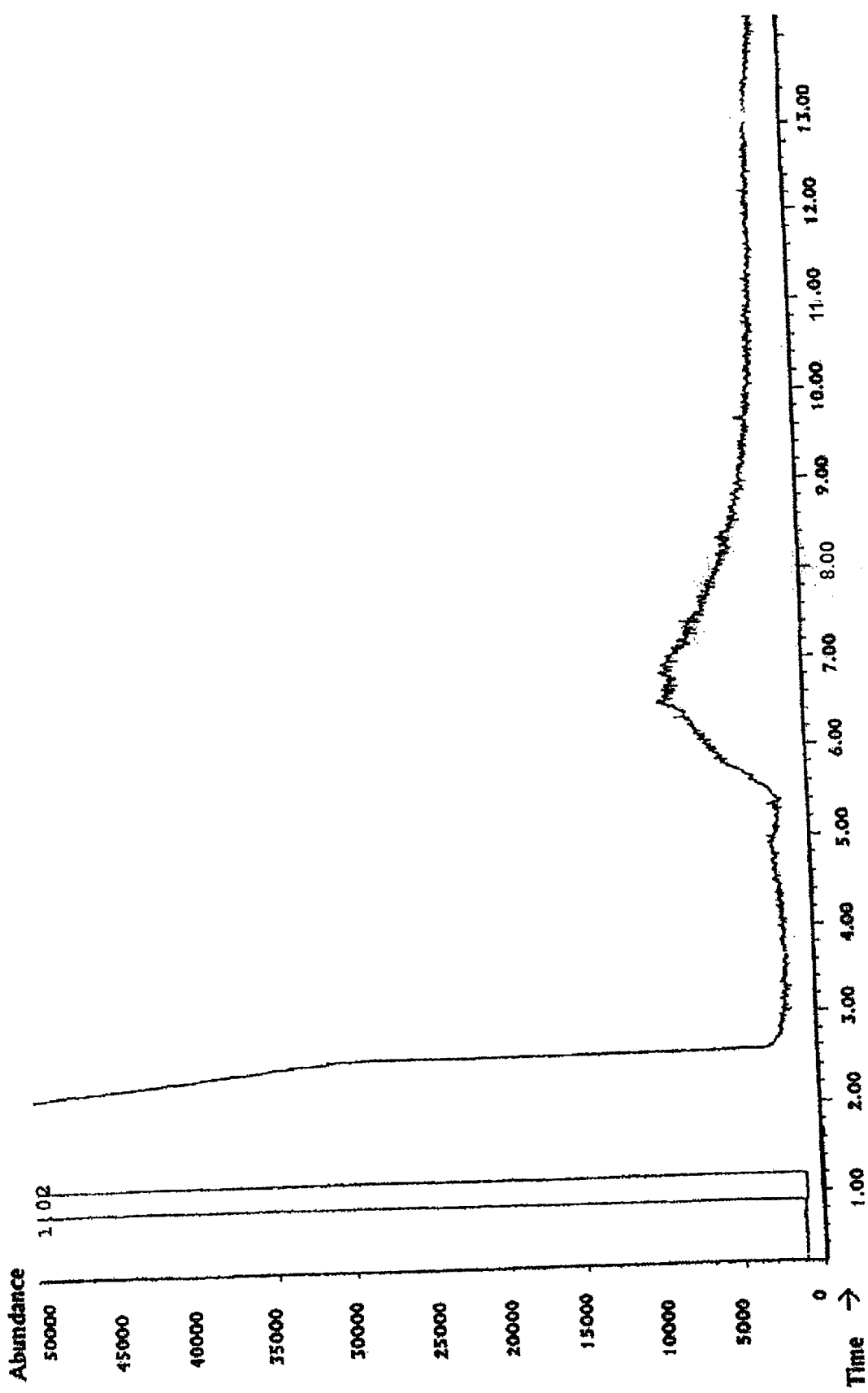
FIG. 5 is a chromatogram of a sample collected above a concentrated fatty acid solution covered with one inch of an oil containing activated carbon

FIG. 5 is the chromatogram of a sample collected above the same fatty acid solution, now covered with one inch of the same oil as in the FIG. 4 sample but containing activated carbon in an oil to carbon ratio of approximately 5:1. Once again, it can be seen that the concentration of fatty acids in the headspace above the liquid waste 16 is diminished even further than the sample having only oil applied and the untreated sample.

Figure 6:
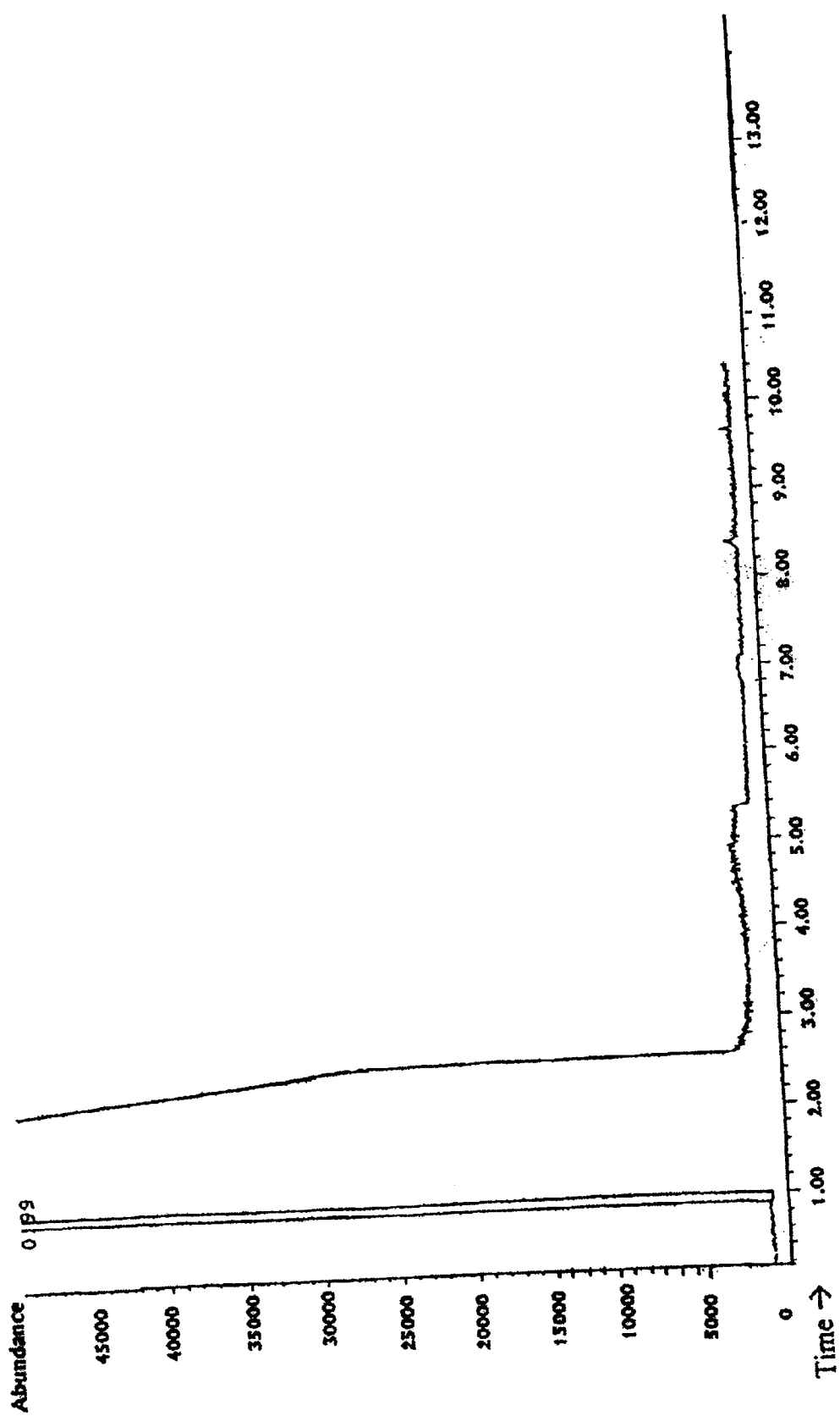
FIG. 6 is a chromatogram of a sample collected above a concentrated fatty acid solution covered with one inch layer of oil containing activated carbon and treated with an ammonia base buffering agent.

FIG. 6 is the chromatogram of a sample collected with the same fatty acid solution covered with a one inch layer of the same oil and activated carbon as in the FIG. 5 sample, and further treated with an ammonia base buffering agent. This chromatogram also shows the progression of diminishing concentration of the fatty acid in the headspace above the liquid waste 16, to the point where the fatty acids are undetectable in FIG. 6.

Figure 7:
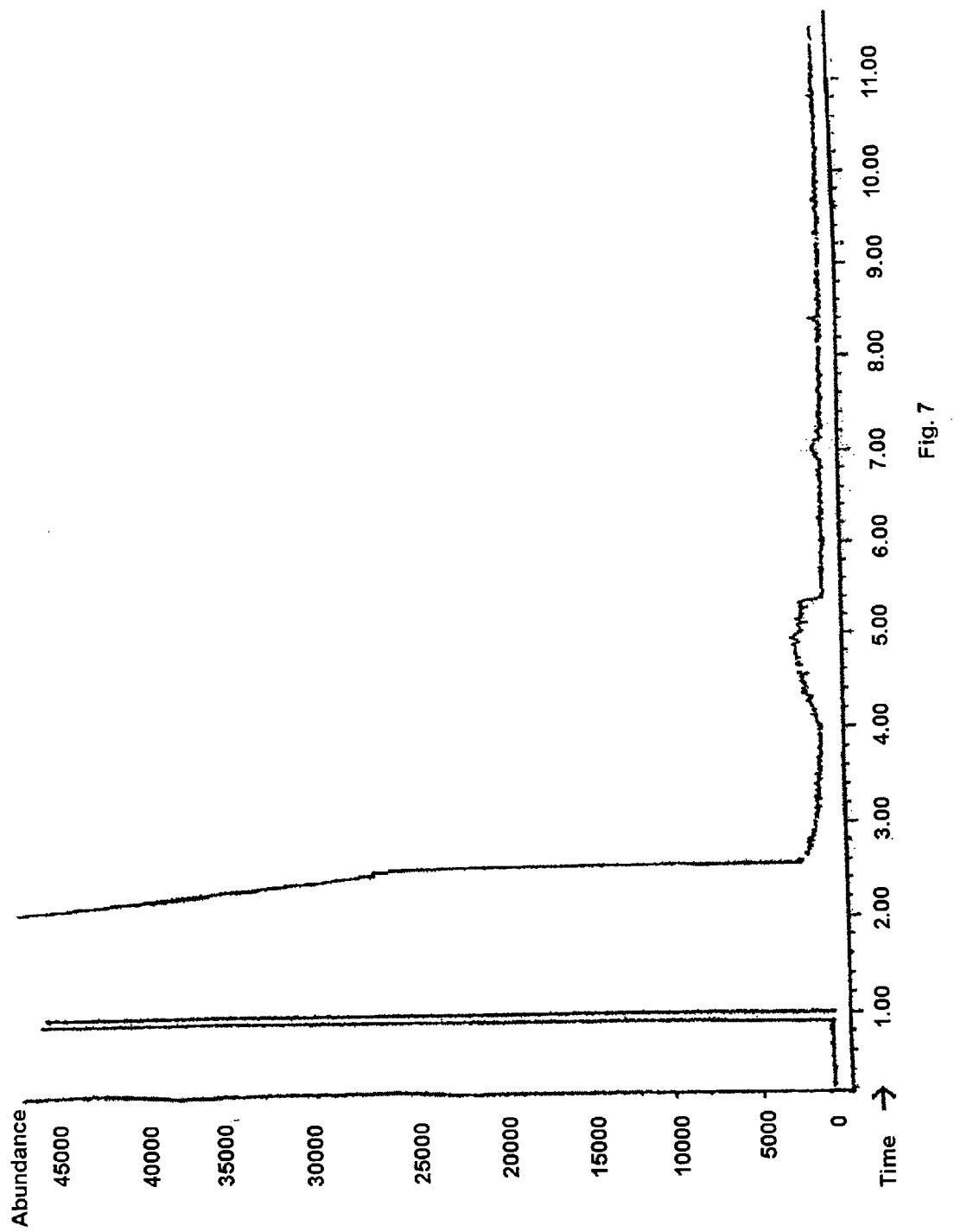
FIG. 7 is a chromatograph of regular laboratory air.

As another base-line or control test, FIG. 7 shows a chromatograph of a sample of laboratory air without any sample contained in the testing room. This test remarkably shows that the emissions for the treated sample, shown in FIG. 6, are virtually identical to those of regular laboratory air.

The method advantageously includes the following steps: applying a layer of oil at least one inch in depth to the surface of animal waste; and injecting a base buffering agent into the animal waste. The layer of oil preferably contains an amount of activated carbon resulting in an oil to carbon ratio of approximately 5:1. The base buffering agent is preferably ammonia with ammonium chloride. While not critical to the described method, it is advantageous to pump the waste present in the pit or other container down to a minimal level prior to applying the layer of oil.

While the above description refers to waste from mega hog farms, it should be understood that the waste may be any organic waste from which foul or noxious odors are emitted. Examples include portable toilets as well as barns; and sewage containing human waste as well as animal waste on a farm. As used herein the terms "waste water" or "waste" should be understood in this broad context.

Other objects, features and advantages will be apparent to those skilled in the art. The invention in its broader aspects is not limited to the specific steps and apparatus shown and described but departures may be made therefrom within the scope of the appended claims without departing from the principles of the invention and without sacrificing the chief advantages.

We claim:

1. A method of treating digestible and odiferous waste, including both liquid and solid waste matter, in a containment system to minimize odors, including the step of applying a layer of a vegetable oil and activated carbon to the surface of the digestible and odiferous waste.

2. A method of treating digestible and odiferous waste in a containment system to minimize odors as set forth in claim 1, wherein the vegetable oil used is corn oil.

3. A method of treating digestible and odiferous waste in a containment system to minimize odors, including the step of applying a layer of oil including activated carbon to the surface of the digestible and odiferous waste, wherein the ratio of oil to activated carbon in the layer of oil is approximately 5:1.

4. A method of treating digestible and odiferous waste in a containment system to minimize odors as set forth in claim 1, wherein the layer of oil is at least one inch in depth.

5. A method of treating digestible and odiferous animal waste in a containment system to minimize odors emitting therefrom, including the steps of:
    applying a layer of an oil to the surface of the digestible and noxious animal waste; and
    injecting a base buffering agent into the digestible and odiferous waste.

6. A method of treating digestible and odiferous animal waste in a containment system to minimize odors as set forth in claim 5, wherein the base buffering agent is composed of ammonia with ammonium chloride.

7. A method of treating digestible and odiferous livestock waste in a containment system of a livestock holding facility to minimize odors including the steps of:
    collecting a volume of digestible and odiferous livestock waste including both liquid and solid matter into the containment system;
    applying a layer of oil and activated carbon mixture to the surface of the digestible and odiferous livestock waste; and
    injecting a base buffering agent into the digestible and odiferous livestock waste.

8. A method of treating digestible and odiferous waste in a containment system to minimize odors as set forth in claim 7, wherein the ratio of oil to activated carbon is approximately 5:1.

9. A method of treating digestible and odiferous waste in a containment system to minimize odors as set forth in claim 7, wherein the layer of oil is at least one inch in depth.

10. A method of treating digestible and odiferous waste in a containment system to minimize odors as set forth in claim 7, wherein the oil used is a vegetable oil.

11. A method of treating digestible and odiferous waste in a containment system to minimize odors as set forth in claim 10, wherein the vegetable oil used is corn oil.

12. A method of treating digestible and odiferous waste in a containment system to minimize odors as set forth in claim 7, wherein the base buffering agent is ammonia with ammonium chloride.

13. A method of treating digestible and odiferous waste in a containment system to minimize odors including the steps of:
    a holding the digestible and odiferous waste in a containment system so that the waste has an upper surface;
    preparing a mixture of corn oil and activated carbon in a ratio of approximately 5:1;
    applying a layer of the corn oil and activated carbon mixture onto the upper surface of the digestible and odiferous waste and to a depth of about at least one inch; and
    injecting a base buffering agent composed of ammonia with ammonium chloride into the digestible and odiferous waste below the level of the corn oil and activated carbon mixture.

14. The use of a layer of oil and activated carbon in conjunction with a base buffering agent in amounts suitable to control odors from digestible and odiferous waste in a containment system including the steps of applying the layer of oil and activated carbon to the surface of the digestible and odiferous waste and injecting the base buffering agent into the digestible and odiferous waste below the surface thereof and in an amount to control the pH level to maintain an anaerobic environment.

15. The use as set forth in claim 14, wherein the oil is a vegetable oil.

16. The use as set forth in claim 14, wherein the oil is corn oil.

17. The use as set forth in claim 14, wherein the ratio of oil to activated carbon is approximately 5:1.

18. The use as set forth in claim 14, wherein the base buffering agent is ammonia with ammonium chloride.

19. An apparatus for applying an odor control treatment to digestible and odiferous waste, including:
    a starter plank;
    a pump connected with a treatment source;
    a low pressure manifold mounted on the starter plank and communicating with the pump;
    a plurality of delivery pipes communicating with the low pressure manifold;
    a plurality of hinge points connected with the starter plank;
    a hinge rod pivotally connected with the hinge points;
    a flotation board connected with the hinge rod and located below the delivery pipes,
whereby the treatment flows from the delivery pipes onto the flotation board and then flows off the flotation board onto the digestible and odiferous waste.

20. A waste treatment retainer system, including:
    a waste container with a bottom surface, and wherein the bottom surface is provided with a drain hole;
    a drain pipe extending through the drain hole, a portion of the drain pipe extending into the waste container forming a lip within the waste container;
    a vent pipe with an inside diameter greater than the outside diameter of the drain pipe and surrounding the lip and provided with a means for allowing digestible and odiferous waste to flow from a level below the lip, into the vent pipe, and into the drain pipe;
    a ball with a diameter greater than the inside diameter of the drain pipe and less than the inside diameter of the vent pipe and located within the vent pipe and above the drain pipe;
    a pull cable attached to the ball whereby the ball may be lowered into contact with the lip, sealing the drain pipe, or raised to a position above the drain pipe, allowing digestible and odiferous waste to flow between the bottom of the vent pipe and the lip and exit the waste container through the drain pipe.

* * * * *